United States Patent [19]
Libor et al.

[11] Patent Number: 4,600,744
[45] Date of Patent: Jul. 15, 1986

[54] PROCESS FOR THE PREPARATION OF CLAY MINERAL-CONTAINING GELS WITH STABILIZED STRUCTURE AND REVERSIBLE WATER ABSORPTION ABILITY

[75] Inventors: Oszkár Libor; Gábor Nagy; Tamás Székely, all of Budapest, Hungary

[73] Assignee: MTA Termeszettudomanyi Kutato Laboratoriumai, Budapest, Hungary

[21] Appl. No.: 664,843

[22] Filed: Oct. 25, 1984

[30] Foreign Application Priority Data

Aug. 6, 1984 [HU] Hungary ............................. 1680/83

[51] Int. Cl.$^4$ ................................................ C08K 3/34
[52] U.S. Cl. ...................................... 524/446; 524/448
[58] Field of Search .............................. 524/446, 448

[56] References Cited

U.S. PATENT DOCUMENTS

| | | | |
|---|---|---|---|
| 3,687,846 | 8/1972 | Lang ................................. | 524/446 |
| 3,759,729 | 9/1973 | Fahn ................................. | 524/446 |
| 4,351,754 | 9/1982 | Dupre ............................... | 524/446 |
| 4,480,067 | 10/1984 | Vio .................................. | 524/446 |
| 4,500,670 | 2/1985 | McKinley ......................... | 524/446 |
| 4,503,170 | 3/1985 | Drake .............................. | 524/446 |

*Primary Examiner*—Paul R. Michl
*Attorney, Agent, or Firm*—Keil & Weinkauf

[57] ABSTRACT

The invention relates to a process for the preparation of clay mineral-containing gels with stabilized structure and reversible water absorption ability.

According to the invention an aqueous suspension containing a thixotropic, activated, swelling clay mineral of three-layer structure and/or a swelling chain silicate is treated with a water soluble polymer capable of reacting with the clay mineral and/or chain silicate, the clay mineral:polymer:water ratios are determined at which the resistance of medium of the resulting suspension is at least ten times higher than that of the initial, polymer-free suspension, and then the components are reacted with each other in the pre-determined ratios.

11 Claims, 1 Drawing Figure

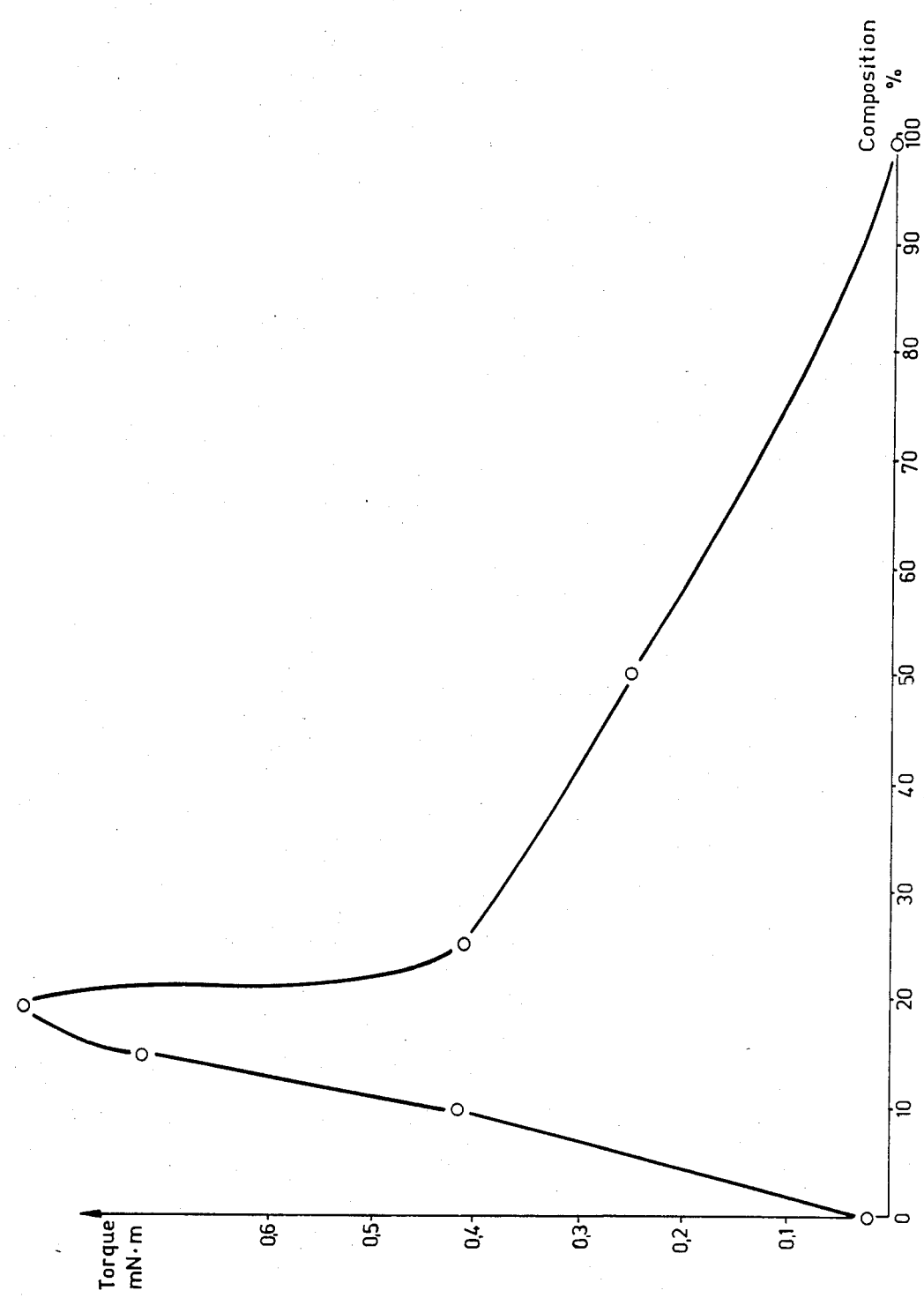

PROCESS FOR THE PREPARATION OF CLAY MINERAL-CONTAINING GELS WITH STABILIZED STRUCTURE AND REVERSIBLE WATER ABSORPTION ABILITY

The invention relates to a method for the preparation of clay mineral-containing gels with stabilized structure and reversible water absorption ability by reacting a clay mineral with an organic polymer. The invention also relates to clay mineral-containing gels prepared by the method of the invention.

It is known that clay minerals react with certain organic polymers by forming various clay-organic complexes (B. K. G. Theng: I. The Chemistry of Clay-Organic Reactions, Halsted Press, 1974; II. Polymer-Clay Complexes, Halsted Press, 1979). Such reactions were utilized for various technical purposes. Thus, e.g. it is known that the rheological properties of clay minerals can be modified by admixing them with polymers; this phenomenon is utilized primarily to improve the characteristics of muds (U.S. Pat. Nos. 577,588, 693,839, and 250,619; Japanese Patent No. 139,800). It is also known that water soluble polymers an be applied to destabilize or flocculate clay mineral suspensions (U.S. Pat. Nos. 3,511,778, 3,701,417, 3,276,998 and 3,052,595; British Pat. No. 1,387,744; Japanese Pat. No. 081,442). Other publications deal with the utilization of clay mineral-polymer reactions in the production of retention or coating materials for paper industry (Swiss Pat. No. 561,668; British Pat. No. 1,010,828). Mixtures or reaction products of clay minerals, organic polymers and other additives can also be applied to produce mortars for undergound insulation (U.S. Pat. No. 4,043,827), to render soil layers water-proof (U.S. Pat. No. 3,772,893), as additives for brick production (U.S. Pat. No. 4,148,662), furthermore for mechanical dehydration and insulation purposes (U.S. Pat. No. 442,161).

It is a common characteristic of a part of the methods disclosed in the above publications that polymers are contacted with non-swelling clay minerals or with clay minerals incompletely disintegrated to elementary lamellae or chains. Under such conditions chemical bonds may form between the clay mineral packages and the polymer chains or balls only on the contacting surfaces. The other part of the known methods has the common characteristic that swollen or quickly swelling clay minerals are reacted with a small amount of polymer. In both instances products consisting of inorganic and organic macromolecules are formed, the structure and gelling properties of which are determined primarily by the given characteristics of the inorganic component, the organic component only modifying these properties to a greater or lesser extent. As an example, when a thixotropic, swelling clay mineral of three-layer structure is reacted in non-disintegrated state with an aqueous solution of a known water soluble polymer, the resulting product still remains thixotropic, and the gel formed from the product peptizes like the starting clay mineral; the polymer present modifies only certain other properties (e.g. water absorption capacity, liquid limit etc.) of the peptizing gel to a greater or lesser extent.

No method has been disclosed so far in the literature which would allow the irreversible fixation (stabilization) of the gel structure of initially thixotropic clay minerals so as to result in a gel having a reversible water uptake/water release ability without any thixotropic character and peptizing ability.

Now it has been found that when a suspension of appropriate concentration of a thixotropic clay mineral, i.e. a swelling smectite with three-layer structure and/or a swelling chain silicate is contacted with a reactive polymer in activated state, i.e. in a form where the bulk of the clay mineral or chain silicate is disintegrated to its elementary lamellae or chains, the elementary lamellae or chains of the clay mineral are joined to the polymer chains by chemical bonds and/or via adsorption, the lamellae "get stringed" on the polymer, and thus the gel structure of the clay mineral is fixed irreversibly. The resulting gel is no longer thixotropic, i.e. its gel structure cannot be destroyed by mechanical effects, furthermore, the gel does not peptize and takes up and releases water in a reversible manner.

Based on the above, the invention relates to a method for the preparation of clay mineral-containing gels with stabilized structure and reversible water absorption ability. According to the invention one proceeds as follows:

In a first series of tests the clay mineral:polymer:water ratios are determined under which the formation of a gel with the required characteristics takes place. To determine these useful limits, aqueous suspensions of varying concentration are prepared from an activated, thixotropic, swelling clay mineral of three-layer structure and/or swelling chain silicate, (in the following: clay mineral), the resistance of medium of the resulting suspensions is measured, thereafter, in a series of tests a reactive water soluble polymer is added to the suspensions either as such or in an aqueous solution, the resistance of medium of the resulting mixtures is measured, and the clay mineral:polymer:water ratios are determined at which the resistance of medium of the suspension is at least ten times higher than that of the initial, polymer-free suspension. Thereafter the clay mineral and the polymer are contacted with one another in a ratio falling within the useful limits determined above and in the presence of an amount of water within the useful limits, and the required ratios are adjusted in one or more steps.

One may proceed so that the clay mineral is reacted with the polymer in a ratio falling within the useful limits, in the presence of an amount of water within the useful limits, whereupon the gel with the required characteristics is formed directly. One may, however, also react the clay mineral with the polymer in the presence of more water than that corresponding to the useful limits, and the clay mineral:polymer ratio may also be outside the useful limits in this first step. In such instances the reaction product flocculates from the aqueous medium. The water content of the flocculate is then decreased mechanically to fall within the useful limits, and, if necessary, the clay mineral:polymer ratio of the mass is adjusted simultaneously to fall within the useful limits by adding further amount(s) of clay mineral and/or polymer to the mass. The mechanical dehydration is generally performed by kneading. In this instance the gel with the required characteristics is obtained after the mechanical dehydration step.

It should be noted that a single polymer or mixtures of two or more polymers can equally be utilized in the method of the invention. When the gel with the required characteristics is produced in two steps, and a polymer is also added to the mass during the mechanical dehydration, the polymers utilized in the first and second steps may be the same or different.

If desired, the water content of the resulting gel can be removed partially or totally. When all the water present is removed, a xerogel powder is obtained. If desired, this partially or totally dried gel can be reacted in a subsequent step with a further amount of a polymer. This reaction is performed in an aqueous medium, under keeping the clay mineral:polymer ratio still within the useful limits. By this step the properties of the gel can be modified. Of course, other known organic and/or mineral additives can also be added to the gel in order to modify its final properties.

Of the thixotropic, swelling clay minerals with threelayer structure the montmorillonite-type clay minerals, such as beydellite, hectorite, sepiolite and nontronite are preferred. These clay minerals can be utilized either alone or in admixture with one another. Of the thixotropic, swelling chain silicates attapulgite is to be mentioned; this clay mineral can be utilized either alone or in admixture with the three-layer clay minerals listed above. The clay minerals can also be applied in the form of clay mineral-containing rocks (e.g. bentonite); according to our experiences the non-clay mineral constituents of the rock do not disturb the reaction, and may sometimes favourably influence the characteristics (e.g. strength or elasticity) of the gel formed. The term "clay mineral" used in the specification and claims also covers such clay mineral-containing rocks. The dry substance content of the aqueous clay mineral suspension may be preferably 1 to 20% by weight, particularly preferably 3 to 15% by weight.

It is of basic importance that the clay minerals should be utilized in activated state. The term "activated clay mineral" covers swollen clay minerals, which contain mainly $H^+$, $Na^+$, $Li^+$ and/or $NH_4^+$ ions as loosely bound, exchangeable interlamellar cations. The clay minerals or clay mineral-containing rocks can be activated by methods known per se.

The reactive polymers, i.e. the water soluble polymers capable of reacting with clay minerals are known per se; of them the water soluble polymers containing —COOH, —COO$^-$M$^+$ (M$^+$ is a monovalent cation), —CONH$_2$, —OH and/or

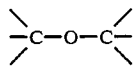

groups as functional groups are to be mentioned. The reactive polymers may be e.g. the following: polyacrylamide, polymethacrylamide, polyacrylic acid, polymethacrylic acid, hydrolysed polyacrylamide, acrylamide-acrylic acid copolymers, hydrolysed acrylamide-acrylate copolymers, polyvinyl alcohol-acrylic acid copolymers, polyvinyl alcohols, hydrolysed polyvinyl esters, polyethylene oxides, water soluble polysaccharides etc., and mixtures thereof. Graft copolymers can also be applied, of them copolymers containing acrylic acid, methacrylic acid, acryl amide and/or methacryl amide side chains grafted onto a cellulose chain are to be mentioned.

The molecular weight of the polymers usable in the method of the invention may vary generally between 50,000 and 20,000,000, preferably between 500,000 and 10,000,000. According to our experiences the greater the molecular weight of the polymer, the smaller amount of polymer is sufficient to stabilize the gel structure of the starting activated clay mineral irreversible.

It is also of basic importance that the polymer(s) should be reacted with the clay mineral(s) in a sufficiently large amount of water, since it can be ensured only in this case that the polymer balls are sufficiently run off and join to the elementary clay mineral chains or lamellae to fix their structure. It is preferred to add the polymer as an aqueous solution to the aqueous suspension of the clay mineral.

By the appropriate choice of the clay mineral:polymer weight ratio and the molecular weight of the polymer, gels preferably with a viscosity exceeding 100,000 cP at 20° C. are prepared. The clay mineral:polymer weight ratios as well as the molecular weight of the polymer required to attain this viscosity can be determined by the test described above.

Various techniques can be applied to contact the clay mineral suspension with the polymer or its aqueous solution. One may e.g. simply admix the suspension with the polymer or its aqueous solution. It is more preferred, however, to admix the clay mineral suspension with the aqueous solution of the polymer in a spray head and then spraying the mixture. Alternatively, the aqueous solution of the polymer and the aqueous suspension of the clay mineral may be sprayed from two separate spray heads, whereupon the droplets contact one another in the air. Using this latter method, the gel structure is stabilized simultaneously with the partial or total drying of the gel.

As mentioned above, various filling agents or modifying agents (e.g. natural or synthetic fibrous materials, inert or activated particulate fillers, such as quarz sand or ground basalt, hydraulic binding agents, such as alkaline fly ash, etc.) can be added, if desired, to the gel in order to modify the properties of the end-product. These filling and modifying agents are nown per se. Depending on their chemical nature, the filling or modifying agents can be added to the clay mineral suspension (i.e. to the gel with non-stabilized structure), to the wet, stabilized gel or to the partially or totally dried stabilized gel.

A major advantage of the method according to the invention is that a stable gel structure can be formed even when reacting the clay mineral with a relatively small amount of polymer. Upon stabilizing the gel structure, the utilization fields of the starting clay mineral can be broadened to a great extent. Thus, e.g. the gels prepared according to the invention can be utilized as water-insulating materials particularly in the building industry (primarily as insulators for structural engineering); as rock strenghening and water insulating agents in the mining industry; for the environment-proof insulation and closing of waste containers; in the agriculture, primarily to increase the water retention ability of loose sandy soils; as soil stabilizing agents; for fire extinguishing, etc.

The invention is elucidated in detail by the aid of the following non-limiting Examples.

EXAMPLE 1

An aqueous suspension of 10% by weight dry substance content is prepared from commercially available activated bentonite (B1 type bentonite, produced by Erbslöh Co., Germany) under laboratory conditions. The suspension is sampled, and the sample is filled into a Brabender type rheometer. The torque of the cone which rotates in the rheometer is measured at 20° C.; the measured torque is characteristic of the resistance of medium. Then, varying amounts of polyacrylamide (average molecular weight: 3,000,000) are added, as an 5% aqueous solution, to the suspension samples, the suspensions are admixed with the solution, and the torques of the mixtures are measured again. The measured torques are plotted against the weight ratio of the polymer in the mixture (see FIG. 1). It can be seen from the curve that, with the water content applied in the test, a clay mineral:polymer weight ratio of 95:5 to 43:54 should be maintained in order to obtain a non-thixotropic, non-peptizing gel with stabilized structure, which has reversible water absorption ability.

In the following the ratios determined as described above are maintained when preparing a gel.

EXAMPLE 2

1000 g of an aqueous suspension, containing 10% by weight of activated bentonite defined in Example 1, are prepared under laboratory conditions. In the following, 50 g amounts of the thixotropic substance, swollen to equilibrium, are reacted with the polymers listed in Table 1.

TABLE 1

| No. of solution | Polymer | Average mol. weight, millions | Concentration of the solution, % |
|---|---|---|---|
| B1 | Polyacrylamide | 10 | 0.2 |
| B2 | Polyacrylamide | 3 | 0.5 |
| B3 | Polyacrylamide | 0.3 | 2 |
| B4 | Hydrolysed polyacrylamide (hydrolysis degree: 3%) | 0.8 | 2 |
| B5 | Hydrolysed polyacrylamide (hydrolysis degree: 40%) | 10 | 0.1 |
| B6 | Hydrolysed polymethacrylamide (hydrolysis degree: 10%) | 1 | 0.8 |
| B7 | Acrylamide - acrylic acid copolymer (acrylamide content: 20%) | 2 | 0.5 |
| B8 | Acrylamide - maleic anhydride copolymer (alternating) | 0.5 | 3 |
| B9 | Hydrolysed vinyl acetate - acrylic acid copolymer (acrylic acid content: 20%) | 0.7 | 2 |
| B10 | Hydrolysed methacrylate - methacrylic acid copolymer (containing maximum 10% of non-hydrolysed ester groups) | 0.5 | 4 |

The polymers are utilized as aqueous solutions. Each of the polymer solutions has a viscosity exceeding 500 cP at 20° C. 20 ml of a polymer solution are admixed with 50 g of a bentonite gel in a breaker of 100 ml capacity. After 10 to 60 seconds the viscosity of the mixture increases abruptly, and a stable gel is formed. The strength of the gel is such that it can be removed from the beaker in a single piece and does not break under its own weight.

All the resulting gels are water-insoluble, they take up and release water reversibly, and do not show syneresis.

The limiting values of the clay mineral:polymer weight ratios were determined according to the test described in Example 1; the weight ratios listed in this Example are within the limiting values.

EXAMPLE 3

One proceeds as described in Example 2 with the difference that a homogeneous mixture of 10 ml each of solutions B1 and B9 is added to the bentonite suspension. The reaction of the two polymers with the clay mineral takes practically the same time, and an apparently homogeneous gel is formed within about 1 minute. The resulting gel is, however, heterogeneous, i.e. the clay mineral lamellae are fixed by two polymeric matrices different in chemical structure. The properties of the gel are the same as given in Example 2.

EXAMPLE 4

A 6% by weight aqueous suspension is prepared from commercially available activated bentonite of type F1 (produced at Mäd, Hungary). Aliquots of the suspension are admixed with the filling agents listed in Table 2.

TABLE 2

| No. of filler | Filler | Amount of filler (% by weight, calculated for the suspension) |
|---|---|---|
| A1 | Quarz powder (type 00) | 10 |
| A2 | Asbestos wool (fibre length: 0.5–1.5 mm) | 2 |
| A3 | Dry sodium cellulose | 3 |
| A4 | Cement powder (admixable with bentonites | 4 |

The resulting suspensions are admixed with polymer solution B5 (see Example 2) in a weight ratio of 5:2. The compression strength and resistance to crack of the resulting gels improve significantly upon the effect of the filling agents; the compression strength of the resulting gels is 2–3-fold of that of the non-filled one. These filler-containing gels can be applied primarily for the production of water-insulating screens.

EXAMPLE 5

The bentonite suspension defined in Example 2 and polymer solution B4 defined in Example 2 are introduced simultaneously in a volume ratio of 5:2, through a mixing tube, into the upper part of a filled geyser dryer, at an inlet 10 cm below the glass bead filling. The filling is moved in the centre by a pulley stirrer, and is kept floating by a hot (120° C.) air stream introduced at the bottom of the dryer. The liquid substance, entering through the mixing tube, is deposited on the filling and gellifies simultaneously, thereafter the thin gel layer dries, comminutes, and a fine xerogel powder separates in the cyclon part. The resulting fine powder, with an average particle size of about 50 μm, is swelling, and has a reversible water absorption ability. The water tightness of the resulting gel is far lower than that of the initial bentonite (the K value of the initial bentonite is in the order of $10^{-8}$, whereas that of the gel only about $10^{-10}$). The drying temperature should be so controlled that the average temperature of the particles does not exceed 90° C.

EXAMPLE 6

The swollen bentonite suspension of the composition given in Example 4 and the aqueous polymer solution B1 defined in Example 2 are introduced simultaneously, in a volume ratio of 4:1, into an Anhydro type disc spray dryer. The sprayed droplets gellify, and a fine xerogel powder, with an average particle size of 20 μm, separates in the cyclon. The properties of the resulting product are very close to those of the xerogel obtained according to Example 5. The drying temperature should be so controlled that the average temperature of the particles does not exceed 90° C.

EXAMPLE 7

8 g of the xerogel powder prepared according to Example 6 are suspended in 92 ml of distilled water, and 20 ml of a polymer solution B1, defined in Example 2, are added to the suspension with stirring. After about 30 seconds of stirring a stable gel is obtained, with an elongation at rupture of about 200%.

EXAMPLE 8

One proceeds as described in Example 7 with the difference that an 0.5% aqueous solution of a polyethylene oxide (Polyox Coagulant Covale; average molecular weight: about 6 millions) is added to the suspension. After about 40 seconds of stirring a gel is formed, followed by a syneresis stage of about 10% after further 10 minutes. The mechanical strength of the resulting gel is particularly favourable; its elongation at rupture is of aobut 200%, and its strength at rupture is about the double of that of the product obtained according to Example 7.

EXAMPLE 9

The bentonite suspension and the polymer solution described in Example 6 are sprayed simultaneously, from two separate tanks equipped with spray devices, onto the surface of freshly built storm banks subject to heavy soil erosion. Where the droplets form a coherent layer, they are partially adsorbed by the upper surface of the soil and the resulting gel sticks the soil particles together and stabilizes them. The gel layer does not interfere with plant growth. It is also possible to introduce glass seeds or nutrient substances into the polymer solution, to bring them onto the treated surface simultaneously with gel formation.

EXAMPLE 10

0.8 mg of a partially hydrolysed polyacrylamide (degree of hydrolysis: 20%, average molecular weight: above $10^7$) is added, as a 0.1% aqueous solution, to a suspension of 400 mg of technical kaolinite, 50 mg of quartz powder (particle size: below 10 μm) and 650 mg of activated bentonite (type Fl, produced at Mád, Hungary) in 1 liter of water. The suspension is stirred for 2 minutes at a rate of 200 r.p.m., then for 5 minutes at a rate of 20 r.p.m. the resulting flocculate sediments in 15 minutes. The water above the sediment layer is removed, the sediment, 80 ml in volume, is stirred at a rate of 10 r.p.m., and 2% by weight, related to the weight of the bentonite, of the above polymer are added to the sediment as an 0.5% aqueous solution, whereupon the volume of the sediment decreases to 20 ml. 60 ml of water above the sediment are removed, and the sediment is kneaded in the kneading chamber of a Brabender plastograph at a rate of 60 r.p.m. After 10 minutes of kneading a homogeneous gel is formed from the sediment, with a simultaneous loss of water.

What we claim is:

1. A process for the preparation of clay mineral-containing non-thixotropic gels with stabilized structure and reversible water absorption ability, characterized in that
   (a) the resistance of medium of an aqueous suspension sample containing a thixotropic, activated, swelling clay mineral of three-layer structure and/or swelling chain silicate is measured, thereafter in a series of tests a water soluble polymer capable of reacting with the clay mineral and/or chain silicate is added to the suspension samples either as such or in an aqueous solution, the resistance of medium of the resulting mixtures is measured, and the clay mineral:polymer:water ratios are determined at which the resistance of medium of the suspension is at least ten times higher than that of the initial, polymer-free suspension, whereby the useful limits are obtained, then
   (b$_1$) the clay mineral and/or chain silicate is contacted with the polymer in a ratio falling within the useful limits, in the presence of an amount of water within the useful limits, or
   (b$_2$) the clay mineral and/or chain silicate is contacted with the polymer in a ratio within or outside the useful limits, in the presence of more water than that corresponding to the useful limits, the water content of the resulting flocculate is then decreased mechanically to fall within the useful limits, and, if necessary, the clay mineral:polymer ratio of the mass is adjusted simultaneously within the useful limits by adding further amount(s) of clay mineral or chain silicate and/or polymer to the mass,
   and, if desired, the resulting gel is partially or totally dried, whereafter, if desired, the partially or totally dried gel is reacted in an aqueous medium with a polymer capable of reacting with the clay mineral or chain silicate under keeping the clay mineral:-polymer ratio still within the useful limits.

2. A process as claimed in claim 1, characterized in that a suspension containing 1 to 20% by weight, preferably 3 to 15% by weight, of clay mineral and/or chain silicate is used.

3. A process as claimed in claim 1, characterized in that a water soluble polymer containing —COOH, —COO$^-$M$^+$ (wherein M$^+$ is a monovalent cation), —CONH$_2$, —OH and/or

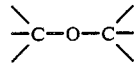

groups as functional groups is used.

4. A process as claimed in claim 3, characterized in that the polymer is used as an aqueous solution with a viscosity of 50 to 100,000 cP at 20° C.

5. A process as claimed in claim 3, characterized in that a polymer with a molecular weight of 50,000 to 20,000,000, preferably 500,000 to 10,000,000 is used.

6. A clay mineral-containing gel with stabilized structure and reversible water absorption ability, whenever prepared according to claim 1.

7. A process as claimed in claim 4 characterized in that a polymer with a molecular weight of 50,000 to 20,000,000, preferably 500,000 to 10,000,000 is used.

8. A clay mineral-containing gel with stabilized structure and reversible water absorption ability whenever prepared according to claim 2.

9. A clay mineral-containing gel with stabilized structure and reversible water absorption ability whenever prepared according to claim 3.

10. A clay mineral-containing gel with stabilized structure and reversible water absorption ability whenever prepared according to claim 4.

11. A clay mineral-containing tel with stabilized structure and reversible water absorption ability whenever prepared according to claim 5.

* * * * *